(12) United States Patent
Myklebust et al.

(10) Patent No.: US 6,351,671 B1
(45) Date of Patent: Feb. 26, 2002

(54) SYSTEM FOR MEASURING AND ANALYZING CARDIO-PULMONARY-RESUSCITATION (CPR) PARAMETERS FOR USE WITH AND BY AN EXTERNAL DEFIBRILLATOR (AED) OR A TRAINING DEFIBRILLATOR

(75) Inventors: Helge Myklebust; Harald Eikeland, both of Stavanger; Trygve Eftestøl, Forus, all of (NO)

(73) Assignee: Laerdal Medical AS, Stavanger (NO)

( * ) Notice: Subject to any disclaimer, the term of this patent is extended or adjusted under 35 U.S.C. 154(b) by 0 days.

(21) Appl. No.: 09/460,240

(22) Filed: Dec. 13, 1999

(30) Foreign Application Priority Data

Dec. 11, 1998 (NO) .............................................. 5822/98

(51) Int. Cl.⁷ .................................................. A61N 1/18
(52) U.S. Cl. ............................................ 607/5; 434/265
(58) Field of Search ................................ 434/262, 265; 607/5, 6, 8, 142

(56) References Cited

U.S. PATENT DOCUMENTS

| | | | |
|---|---|---|---|
| 4,619,265 A | | 10/1986 | Morgan et al. |
| 5,544,661 A | | 8/1996 | Davis et al. |
| 5,662,690 A | * | 9/1997 | Cole et al. ............... 607/5 |
| 5,718,235 A | | 2/1998 | Golosarsky et al. |
| 5,782,878 A | * | 7/1998 | Morgan et al. ............... 607/5 |
| 5,833,711 A | | 11/1998 | Schneider, Sr. |
| 5,951,598 A | * | 9/1999 | Bishay et al. ............... 607/142 |
| 6,097,982 A | * | 8/2000 | Glegyak et al. ............... 607/7 |
| 6,125,299 A | * | 9/2000 | Groenke et al. ............... 607/6 |
| 6,193,519 B1 | * | 2/2001 | Eggert et al. ............... 434/262 |

FOREIGN PATENT DOCUMENTS

| | | |
|---|---|---|
| EP | 0 183 462 | 6/1986 |
| WO | WO 00/27464 | * 5/2000 |

OTHER PUBLICATIONS

Gruben, Kreg G. et al., "System for Mechanical Measurements During Cardiopulmonary Resuscitation in Humans" IEEE Transaction on Biomedical Engineering, vol. 37, No. 2, Feb. 1990, pp. 204–209.

* cited by examiner

Primary Examiner—William E. Kamm
Assistant Examiner—Frances P. Oropeza
(74) Attorney, Agent, or Firm—Nixon & Vanderhye P.C.

(57) ABSTRACT

A system for measuring and analyzing CPR parameters for use with and by an external defibrillator, where a pressure sensitive electrode is connected to a defibrillator, in addition to the standard electrodes of the defibrillator. The information from the pressure sensitive electrode, together with information derived from modulation of the impedance of the thorax, measured by the defibrillator, describes the quality of the CPR performed, and is used to generate voice messages that increase the quality and the effectiveness of the CPR. The defibrillator may in addition be equipped with a transmission device that sets up a radio connection with an emergency center. The emergency center is equipped with a display unit that shows the activities at the resuscitation site. In addition to the data transfer link, a speech connection is set up via a microphone and a speaker on the resuscitation site and a microphone and auditory unit at the emergency center, in order to allow an operator at the emergency center to intervene and direct the attempt at resuscitation during the critical phases following the electrical shocks. During training and practice, the defibrillator or the training defibrillator will receive information from sensors placed in the manikin regarding the CPR performance, and will then use this information to give instructions.

12 Claims, 5 Drawing Sheets

SYSTEM FOR MEASURING AND ANALYZING CARDIO-PULMONARY-RESUSCITATION (CPR) PARAMETERS FOR USE WITH AND BY AN EXTERNAL DEFIBRILLATOR (AED) OR A TRAINING DEFIBRILLATOR

BACKGROUND OF THE INVENTION

The present invention relates to a system for measuring and analyzing Cardio-Pulmonary-Resuscitation (CPR) parameters for use with and by an external defibrillator, including a training defibrillator.

The term external defibrillator covers all types of defibrillators that employ pads to be connected to the outside of the patient's chest. This also includes training defibrillators, the appearance and behavior of which simulate a real defibrillator without being able to discharge defibrillator shocks. Training defibrillators are used with manikins during training and practice. As a comparison, an "internal defibrillator" or so-called implanted defibrillator is a device that is placed underneath the patient's skin, and which has electrodes connected directly to the heart muscle.

For years, the use of defibrillators in the case of sudden cardiac death has been recognized as the only curative treatment. Defibrillation involves the discharge of an electric pulse with relatively high energy (defibrillator shock) through electrodes connected to the patient's chest. Several designs of electrodes exist, but in the main they can be divided into two groups: "Paddles" are electrodes that are held manually on the chest. Adhesive electrodes or "Pads" are electrodes that are attached to the chest by using an adhesive, and which make use of a conducting polymer in order to establish good electric contact with the skin.

External defibrillators use the electrodes to discharge the electrical shock, to measure the patient's EGG, and to measure any impedance. The purpose of the impedance measurement is to determine the degree of electrical connection between the electrodes. If the impedance is close to zero, this would suggest a short circuit between the electrodes. In the opposite case, if the impedance is high, this would imply insufficient contact between the electrodes. Some types of defibrillators use impedance measurements in order to determine the voltage and time for discharging the defibrillator shock, so that the energy delivered to the patient is approximately equal to the desired energy.

Defibrillation may, by its very nature, involve a risk for those who treat the patient, if they touch the patient or in any other way come into contact with the electrodes. Therefore, the procedures for use include making sure everyone is clear before the shock is discharged. A defibrillator will employ voice messages in order to get the user and any assistants to follow procedures.

Traditionally, defibrillation has been carried out by highly trained personnel in hospitals. However, as automated defibrillators have developed over the last ten years and have become significantly easier to use, they have also come to be used outside of the hospitals, primarily by the ambulance services. There is also a clear tendency for defibrillators to be used by the laity before the ambulance reaches the patient. This refers especially to fire-fighters, police, guards and flight crews. Common to all of them is the fact that their profession is non-medical.

The trend today is that so-called patients at risk, for instance patients waiting for heart surgery, may have a defibrillator in their home, which can be operated by family members or others in the local environment in case of an emergency. Combined with giving the family CPR training, this ensures a high state of preparedness, in addition to an extra sense of security for the patient.

Unfortunately, attempts at resuscitation following sudden cardiac death are not always successful. When sudden cardiac death occurs, the outcome will among other things be dependent on all the links of the life-saving chain. These links are: Early notification of the support machinery, early CPR, early defibrillation and early advanced cardiac life support. The first treatment given to the patient is the most important. For the patient, it is of vital importance that the treatment not only be started as soon as possible, but also that the treatment is as effective and efficient as possible. In those cases where the heart does not start beating after the first three shocks given with a defibrillator, the treatment protocol prescribes one minute of CPR. The purpose of the CPR is to provide circulation of blood to the heart muscle, which increases the electrical activity in the heart, which in turn increases the probability of an electrical shock from a defibrillator being able to restart the heart. Thus, it is crucial for some patients that the CPR is administered effectively and correctly.

Operating an automated defibrillator is relatively simple, as today's defibrillators employ voice messages to instruct the user, and the apparatus does not normally have more than two control buttons. Performing CPR correctly is however fairly difficult for those who are inexperienced, as this calls for a command of both method and psycho-motory skills. This despite the fact that the user has gone through training and practice.

It is becoming common practice, both in Norway and abroad, that a MECC (Medical Emergency Communication Center) instructs the user in first aid, including CPR, pending the arrival of the ambulance. This assumes that there is an accessible telephone by the patient, preferably with a speaker function so as to let the user concentrate on the patient without having to hold on to the telephone. However, a shortcoming of this situation is the fact that the MECC does not receive concise and quantitative feed-back regarding the events taking place, but have to interpret the situation as best they can based on the information received over the telephone.

Using a defibrillator and performing CPR on people generally presupposes that the user has gone through training and practice.

Today, all CPR training and practice includes the use of special manikins. These manikins have been constructed so as to allow inflations and chest compressions to be performed roughly in the same manner as on a lifeless person. Most manikins have been fitted with a number of sensors that among other things register lung inflations and chest compressions. This registration is used to provide visual feedback regarding the performance, as well as for generating a report on the performance with a view to certification in accordance with the guidelines. When defibrillator training is carried out, this may happen in two alternative ways: If the practice is non-interactive, the defibrillator or the training defibrillator will be equipped with simple adhesive electrodes that are attached to the manikin's chest. Normally, there will be no interaction or communication between the manikin and the training defibrillator.

Interactive practice will normally entail the use of a real defibrillator and a manikin that for defibrillating purposes behaves as a human being. The general design for such interactive use has the manikin equipped with an internal load resistance connected to the connection points on the manikin's chest. The patient cable from the defibrillator has been designed for connection to the connection points. The load resistance will indicate to the defibrillator that it is connected to a patient. Further, the manikin will be provided with a signal transmitter that simulates the electrical activity of the heart (ECG). The signal transmitter is connected to the load resistance, to ensure that this signal is also available to the defibrillator. Finally, the load resistance is designed in such a way as to enable it to absorb the defibrillator shocks. A sensor connected in series with the load resistance is normally designed to be able to influence the signal transmitter.

SUMMARY OF THE INVENTION

The object of the present invention is to provide a system that enables a person with limited knowledge and skills to perform CPR correctly, efficiently and more effectively, so as to give the patient better treatment and thereby a greater chance of survival.

It is also an object of the present invention to provide a system such that training and practice in the use of defibrillators of the type that measures and analyzes CPR parameters, with accompanying voice messages, may be as realistic as possible.

The information provided by the present invention is used by a defibrillator in order to give corrective voice messages to the user. In addition, this information may be transmitted to a medical emergency communication center (MECC) that will interpret the situation and guide the user during the resuscitation attempt. Moreover, the information collected will contribute towards documenting the treatment, which in turn is important with regards to quality assurance and treatment optimization.

BRIEF DESCRIPTION OF THE DRAWINGS

The following will explain the invention in more detail, with reference to the accompanying drawings, in which FIG. 1 schematically shows a person connected to a defibrillator.

DETAILED DESCRIPTION OF PREFERRED EMBODIMENTS

Figure 1:
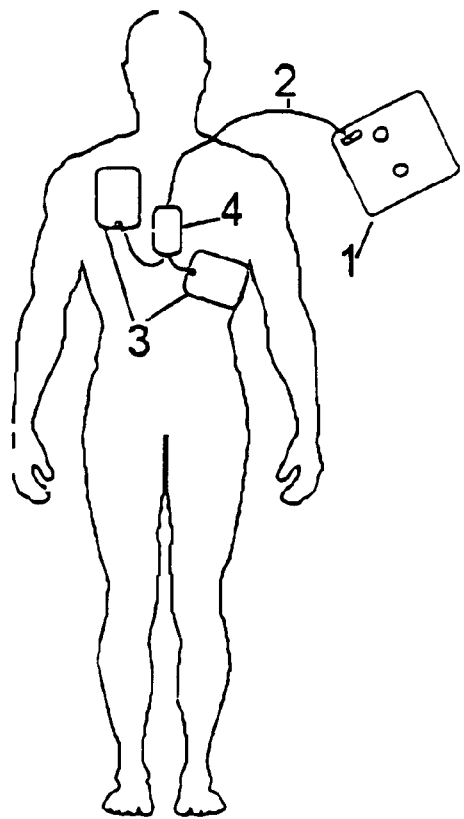

FIG. 1 shows a pressure sensitive pad 4 and electrodes 3 attached to the patient's chest. The top of the pad 4 may be provided with instructions (written text and figures) that tell the user how to position the pad 4, for instance in relation to the patient's nipples. The pad 4 represents an indication of where the hands of the life-saver should be placed for chest compression, and it also functions as a force indicator. The pad 4 will transmit an electrical signal to the defibrillator 1, corresponding to the applied pressure (force). The pad 4 is placed over the patient's heart and attached to the patient's chest in an electrically conducting manner, and forms the signal reference (zero, ground) for the defibrillator's measurements of the ECG signal. This connection improves the quality of the ECG signal, as the charge between the defibrillator and the patient may be balanced through zero instead of through the measuring electrodes, thus reducing the signal interference.

Figure 2:
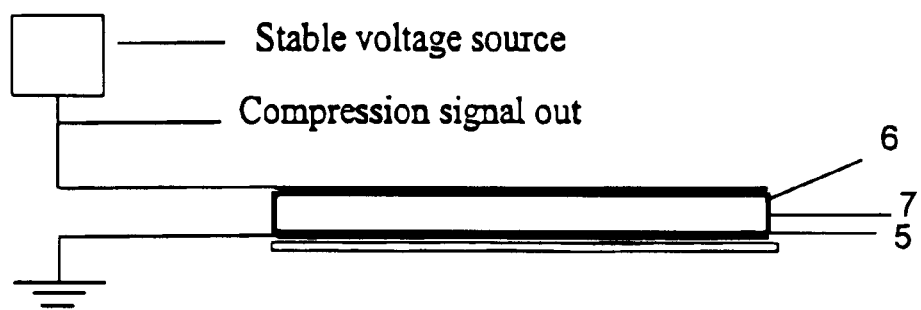
FIG. 2 shows a schematic circuit diagram of the patient connection.

FIG. 2 shows the principles of the pressure pad, which consists of an inner core 7 made from electrically conductive foam or electrically conductive silicone or other practical force sensors. The side facing the patient's body consists of a metal foil 5, in order to ensure that the current is distributed evenly across the area, with an electrically conductive adhesive against the patient's skin. The top of the pressure pad consists of a metal foil 6 with printed instructions and figures, which foil ensures a constant current.

As any pressure on the pad will alter the impedance through the pad, an approximately constant impressed current will give a variable voltage to the processing unit 20 in the defibrillator 1. In its simplest form, an approximately constant current can be achieved by means of series impedance that is significantly greater than the impedance through the pressure pad.

Figure 3:
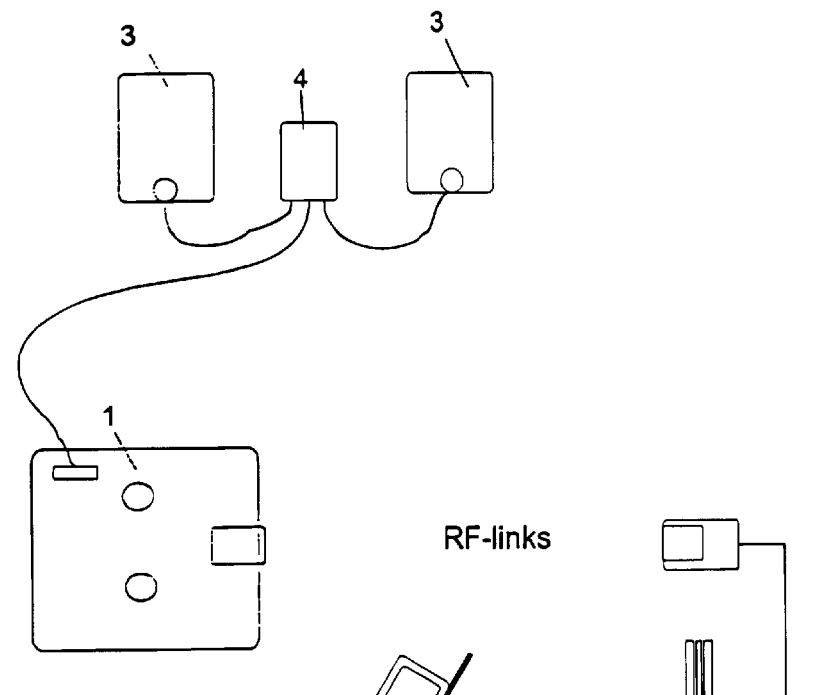
FIG. 3 schematically shows the system according to the invention connected to an emergency center, and a potential display of the information transmitted to the center.
Figure 3:
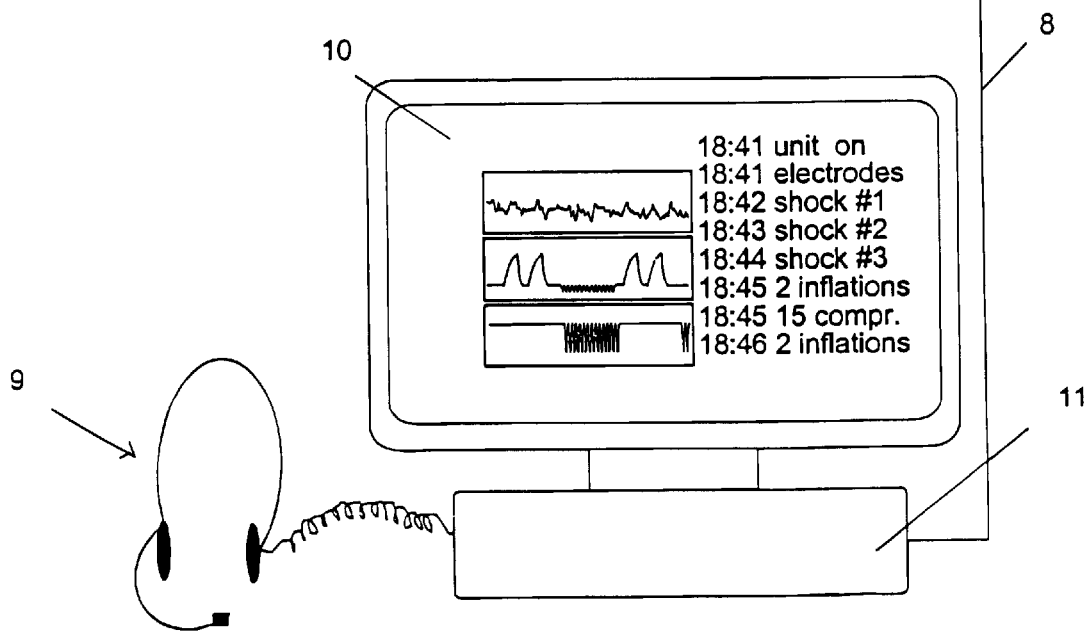
Figure 5:
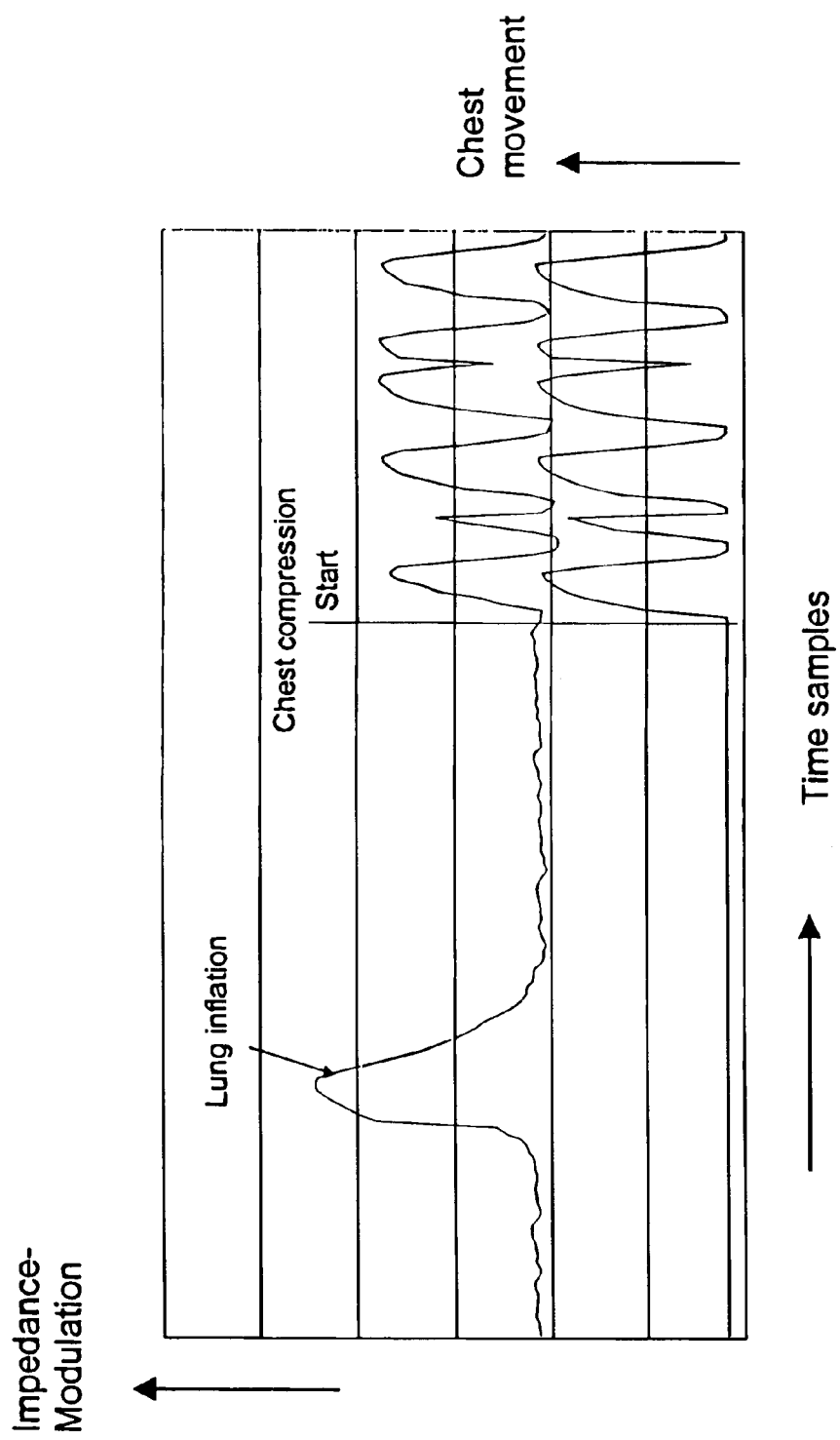
FIG. 5 shows signals measured during resuscitation of a pig, where the upper curve shows the signal proportionally with the impedance modulation, and the lower curve shows the signal proportionally with the depression of the chest.
Figure 6:
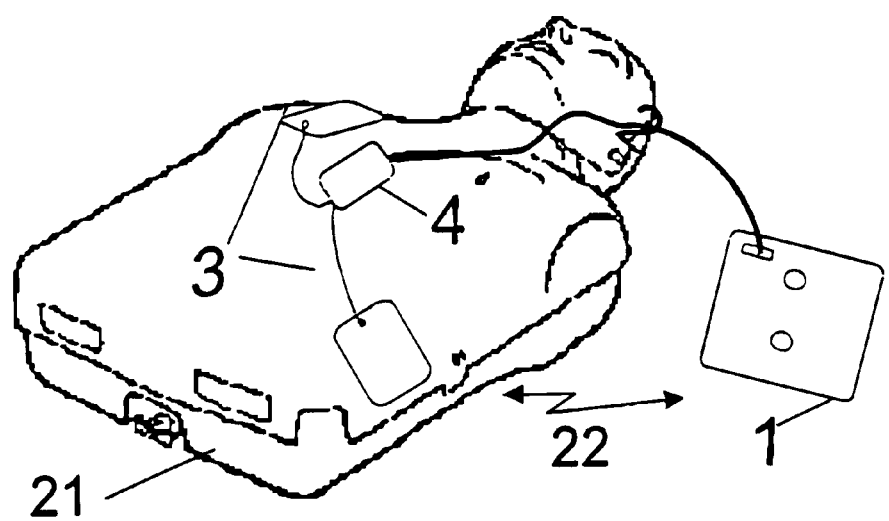
FIG. 6 shows a defibrillator or a training defibrillator connected to a manikin, where the information regarding the CPR performance is communicated between the units.

Standard defibrillator electrodes 3 are used by the impedance system 13 in order to measure the impedance of the thorax (chest), by the ECG-measuring system 12, and by the high voltage system 14 in order to deliver the electrical shock to the patient. The impedance of the thorax is normally measured by supplying an approximately constant alternating current between the defibrillator electrodes 3 and at the same time measuring the alternating voltage between the electrodes 3, which is proportional to the impedance (impedance times current input equals the voltage). The preferred frequency is 30 kHz, but frequencies from 0.1 kHz to 100 kHz may be used. 30 kHz is preferred because the impedance that can be measured at this frequency is close to the impedance that determines the current during discharge of the defibrillator shock. A modulation of the impedance signal, that is a change in the alternating voltage measured between the electrodes at an approximately constant alternating current between the electrodes, is used to calculate CPR parameters. On a lung inflation, the impedance of the thorax increases through the current path being made longer. On chest compression, experiments on pigs show the impedance of the thorax increasing here as well, however the increase is significantly smaller than during lung inflations. When CPR is performed according to the guidelines, two inflations will be given, each lasting 1.5 to 2 seconds, followed by a short break as the life-saver changes position, then 15 chest compressions at a rate of approximately 100/minute, again followed by a short break as the life-saver changes position in order to administer lung inflations. By utilizing this pattern of sequential actions, where the sequential actions are distinctively different, an analysis of the impedance signal in the defibrillator 1 will enable the following CPR parameters to be deduced: Inflation occurrences and inflation time, the occurrence of chest compressions and compression rate, see FIG. 3, in which a screen 10 shows ECG, inflation time and compressions over time respectively; and FIG. 5, which illustrates how lung inflations and chest compressions affect the impedance between the electrodes.

The defibrillator 1 also has a driver and sensor electronics for the pressure sensitive pad (the electrode) 4, the defibrillator 1 being connected to the electrodes 3 and the pad 4 via a cable 2. The signal from the pressure sensitive pad 4 is amplified and filtered before being fed to an analog/digital converter for further analysis and derivation of CPR data, such as compression rate and compression force.

The defibrillator 1 contains a processor 20 that executes an algorithm, e.g. a table of standardized parameters, and based on a comparison with measured CPR parameters, activates a speaking device 15 that informs the user of any mistakes in the CPR, and which contributes towards increasing the quality of the CPR by supplying information regarding the correct magnitude of chest compressions, inflation time, change-over from inflation to chest compression and back to inflation etc.

The algorithms described herein may be in the form of computer programs that compare the measured parameters with standardized methods of treatment according to ILCOR and AHA respectively.

According to the instructions, the defibrillator is only to be used on lifeless persons. The treatment consists of alternating defibrillation (shocks) and CPR according to the following pattern:

Administer three shocks, then one minute of CPR, then three new shocks etc. CPR consists of inflating twice, then performing 15 chest compressions, followed by inflating twice again etc.

The following overview shows typical situations that the defibrillator can monitor and attempt to assist the user in, by means of voice messages:

The data collected, such as ECG, ventilation data, CPR information and other measured data regarding the condition of the patient and the activities carried out on the patient during treatment may, instead of being transferred to a communication center or in addition to the transfer, be stored in a memory 19, from which the data may later be retrieved via e.g. a PC for further evaluation of the CPR that has been performed. Pushbutton indicators 17 are provided to select operations of the defibrillator 1.

Figure 4:
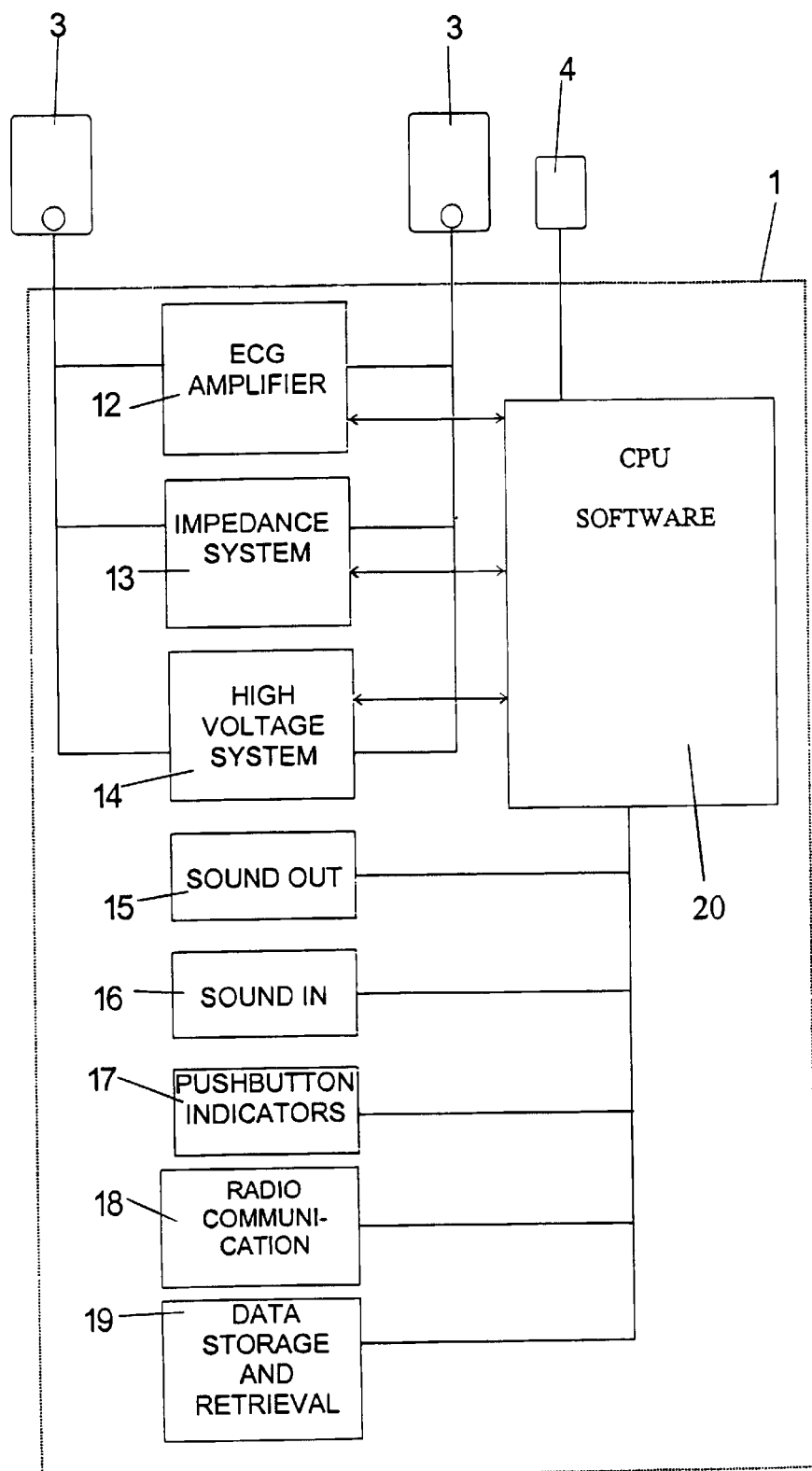
FIG. 4 shows a schematic block diagram of the system according to the invention.

Further, the defibrillator 1 may be provided with a transmitter-receiver device 18 that, when the apparatus is switched on, uses a radio frequency link to connect to and log onto a computer 11 (see FIG. 3) at the MECC via e.g. a mobile telephone or a modem. After connecting, the defibrillator 1 will identify itself and continuously transmit various data such as the ECG signal, chest compression data and inflation data, which is displayed on a screen 10 at the emergency center. Moreover, a speech connection will be established with the supervisory center, in order to allow the defibrillator 1 user to communicate with the emergency center operator 9 via a microphone 16 and a speaker 15 (see FIG. 4). The defibrillator will also be able to receive instructions from the emergency center. In case of such voice communication, the request for speech, e.g. from the emergency center operator, will imply a barring of all other messages from the defibrillator, with the exception of the messages that control the operator's or patient's safety.

This communication will enable the operator to interpret and guide the lifesaving operation. Further, the presence of the MECC operator through voice communication will help

| Situation | Voice message |
|---|---|
| Inflation does not commence | "Inflate twice" or "blow now" or "blow twice" |
| Inflation does not occur despite above messages | "Clear the respiratory passages by bending the head back and lifting the chin" or "remember to pinch the nose shut" |
| Inflation time <1.5 sec | "Take longer" or "not so fast" |
| The second inflation is too long in coming | "Once more" |
| Inflation re-commences too late following 15 compressions | "Blow now" or "blow twice" |
| Compressions do not commence | "Press down between the nipples" |
| Compression rate ≠ 100 ± 10 | "Press faster" / "Not so fast" |
| Compressions re-commence too late following the second inflation | "Start pressing" or "press down on the chest" or "press down 15 times" |

The defibrillator can also start an audible metronome as a guide to the rate of compressions. This may be desirable if the chest compressions interfere with the ECG signal, as a set compression rate makes it easier to filter out the interference, which will keep within a narrow range.

The CPU 20 may also execute an algorithm that calculates the median frequency and the spectral flatness of the filtered ECG signal, and combines the two into a vector, the positive change in magnitude by time of which is compared to a threshold value. If the calculated parameter lies below the threshold value, the defibrillator 1 will recommend a small increase in the compression force. The threshold value is set so as to ensure the quickest possible positive change.

The CPU 20 may also execute an algorithm that calculates the median frequency and the spectral flatness of the filtered ECG signal, and combines the two into a vector, the magnitude of which is compared to a threshold value. When the calculated vector magnitude lies below the threshold value, the defibrillator 1 will recommend CPR, or else it will recommend defibrillation. The threshold value is set so as to ensure the highest possible probability of returning to spontaneous circulation.

make the user feel more secure as he or she is about to perform particularly critical, life-saving first aid. The system may, as a safety precaution, be set up in such a way that communication can only be shut down by the emergency center operator.

By providing the manikin 21 with sensors that register CPR performance and a micro processor that processes and stores that CPR performance, realistic training will be possible through the manikin's micro processor communicating the CPR parameters to the micro processor in the defibrillator. Such communication 22 may take place by means of a cable between the units or by wireless communication if the defibrillator is equipped with bi-directional radio or infrared communication.

What is claimed is:

1. A system for measuring and analyzing CPR parameters for use with and by an external defibrillator or a training defibrillator (collectively hereinafter, "defibrillator"), the system comprising:

a plurality of sensors connected with the defibrillator, the sensors providing information regarding chest compressions and lung inflations;

a system processor communicating with the sensors, wherein the system processor compares the information regarding chest compressions and lung inflations with corresponding parameters that describe guidelines for recommended CPR; and a sound output device connected with the system processor, the system processor driving the sound output device to generate voice messages in response to any deviation between the information regarding chest compressions and lung inflations detected by the sensors and the corresponding parameters that describe guidelines for recommended CPR.

2. A system according to claim 1, further comprising a transmission device that establishes a radio link to an emergency center when the defibrillator is activated in a normal mode, the transmission device effecting a data link that transmits the information regarding chest compressions and lung inflations detected by the sensors and a speech connection link via a microphone and a speaker, thereby permitting an operator at the emergency center to intervene and direct a resuscitation attempt during critical phases following electrical shocks delivered by the defibrillator.

3. A system according to claim 1, further comprising a manikin for operation of the defibrillator in a training mode, the manikin comprising manikin sensors that detect secondary information regarding chest compressions and lung inflations and a manikin sensor processor communicating with the manikin sensors, the manikin sensor processor communicating with the system processor to simulate a connection with an emergency center.

4. A system according to claim 1, wherein the plurality of sensors comprise a pressure sensitive electrode functioning as a force transducer for detecting chest compressions, a top portion of the pressure sensitive electrode being provided with printed electrode placement instructions.

5. A system according to claim 4, wherein the pressure sensitive electrode forms a signal reference for the defibrillator's measurement of an ECG signal.

6. A system according to claim 1, wherein the plurality of sensors comprise an impedance measuring system, and wherein the defibrillator measures a modulation of a voltage generated between electrodes of the defibrillator, the modulation being caused by changes in impedance due to lung inflations and chest compressions.

7. A system according to claim 6, wherein the impedance measurement system communicates an impedance signal to the system processor for determining inflation occurrences, inflation time, occurrences of chest compressions and chest compression rate.

8. A system according to claim 6, wherein an alternating current with a frequency of between 0.1 and 100 kHz is used as an excitation signal.

9. A system according to claim 8, wherein the frequency of the alternating current is 30 kHz.

10. A system according to claim 1, wherein the system processor calculates an ECG signal median frequency and spectral flatness based on the information regarding chest compressions and lung inflations detected by the sensors and combines the ECG signal median frequency and spectral flatness into a vector value, the system processor comparing the vector value to a threshold value, wherein the system processor provides an instruction to proceed with CPR if the vector value is below the threshold and provides an instruction to proceed with defibrillation if the vector value is above the threshold.

11. A system for measuring and analyzing CPR parameters for use with and by an external defibrillator or a training defibrillator (collectively hereinafter, "defibrillator"), the system comprising:

a sound output device;

an impedance modulation sensor connected with the defibrillator, the impedance modulation sensor providing a signal reflecting chest compression, chest compression force, chest inflation and chest inflation time; and a processor communicating with the impedance modulation sensor, the processor determining chest compression, chest compression force, chest inflation and chest inflation time based on the signal from the impedance modulation sensor and comparing with corresponding parameters that describe guidelines for recommended CPR, wherein the processor drives the sound output device to generate voice messages in response to any deviation between chest compression, chest compression force, chest inflation and chest inflation time and the corresponding parameters that describe guidelines for recommended CPR.

12. A method of measuring and analyzing CPR parameters for use with and by an external defibrillator or a training defibrillator (collectively hereinafter, "defibrillator"), the method comprising:

detecting an impedance modulation across electrodes of the defibrillator and providing a signal reflecting chest compression, chest compression force, chest inflation and chest inflation time;

determining chest compression, chest compression force, chest inflation and chest inflation time based on the signal;

comparing the chest compression, chest compression force, chest inflation and chest inflation time with corresponding parameters that describe guidelines for recommended CPR; and generating voice messages in response to any deviation between chest compression, chest compression force, chest inflation and chest inflation time and the corresponding parameters that describe guidelines for recommended CPR.

* * * * *